(12) United States Patent
Schneider (10) Patent No.: US 8,343,208 B2
(45) Date of Patent: *Jan. 1, 2013

(54) STENT HAVING AN EXPANDABLE WEB STRUCTURE

(75) Inventor: Ralph Schneider, Irvine, CA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 12/949,481

(22) Filed: Nov. 18, 2010

(65) Prior Publication Data

US 2011/0125243 A1    May 26, 2011

Related U.S. Application Data

(63) Continuation of application No. 11/601,475, filed on Nov. 16, 2006, now Pat. No. 7,887,578.

(30) Foreign Application Priority Data

Sep. 5, 1998  (DE) .................................. 198 40 645

(51) Int. Cl.
A61F 2/06 (2006.01)
(52) U.S. Cl. ........ 623/1.15; 606/108; 606/195; 606/198
(58) Field of Classification Search .................. 623/1.15; 606/198, 108, 195
See application file for complete search history.

(56) References Cited

U.S. PATENT DOCUMENTS

| | | | |
|---|---|---|---|
| 4,475,972 A | 10/1984 | Wong | |
| 4,580,568 A | 4/1986 | Gianturco | |
| 4,738,740 A | 4/1988 | Pinchuk et al. | |
| 4,743,252 A | 5/1988 | Martin, Jr. et al. | |
| 4,759,757 A | 7/1988 | Pinchuk | |
| 4,776,337 A | 10/1988 | Palmaz | |
| 4,800,882 A | 1/1989 | Gianturco | |
| 4,907,336 A | 3/1990 | Gianturco | |
| 5,015,253 A | 5/1991 | MacGregor | |
| 5,019,090 A | 5/1991 | Pinchuk | |
| 5,041,126 A | 8/1991 | Gianturco | |
| 5,059,211 A | 10/1991 | Stack et al. | |
| 5,102,417 A | 4/1992 | Palmaz | |
| 5,104,404 A | 4/1992 | Wolff | |
| 5,116,360 A | 5/1992 | Pinchuk et al. | |
| 5,122,154 A | 6/1992 | Rhodes | |
| 5,133,732 A | 7/1992 | Wiktor | |

(Continued)

FOREIGN PATENT DOCUMENTS

CA            2309079          11/2004

(Continued)

OTHER PUBLICATIONS

U.S. Appl. No. 10/859,636, mail date Mar. 30, 2011, Issue Notification.

(Continued)

*Primary Examiner* — Vy Q Bui
(74) *Attorney, Agent, or Firm* — Workman Nydegger; Jonathan D. Feuchtwang (57) ABSTRACT

A stent comprises a tubular flexible body composed of a web structure that is expandable from a contracted delivery configuration to a deployed configuration and that comprises neighboring web patterns of alternating concavities extending circumferentially and adjoined by X-shaped transition sections. The web pattern may comprise either arcuate struts interconnected by bends, or a plurality of substantially straight sections with the transition sections formed by the junctions between pairs of adjacent bends of opposite curvatures.

38 Claims, 7 Drawing Sheets

U.S. PATENT DOCUMENTS

| | | |
|---|---|---|
| 5,147,370 A | 9/1992 | McNamara et al. |
| 5,163,951 A | 11/1992 | Pinchuk et al. |
| 5,171,262 A | 12/1992 | MacGregor |
| 5,221,261 A | 6/1993 | Termin et al. |
| 5,282,823 A | 2/1994 | Schwartz et al. |
| 5,292,331 A | 3/1994 | Boneau |
| 5,314,444 A | 5/1994 | Gianturco |
| 5,370,683 A | 12/1994 | Fontaine |
| 5,378,239 A | 1/1995 | Termin et al. |
| 5,380,299 A | 1/1995 | Fearnot et al. |
| 5,421,955 A | 6/1995 | Lau et al. |
| 5,443,458 A | 8/1995 | Eury |
| 5,443,496 A | 8/1995 | Schwartz et al. |
| 5,449,373 A | 9/1995 | Pinchasik et al. |
| 5,449,382 A | 9/1995 | Dayton |
| 5,476,508 A | 12/1995 | Amstrup |
| 5,496,277 A | 3/1996 | Termin et al. |
| 5,514,154 A | 5/1996 | Lau et al. |
| 5,527,354 A | 6/1996 | Fontaine et al. |
| 5,556,414 A | 9/1996 | Turi |
| 5,569,295 A | 10/1996 | Lam |
| 5,591,197 A | 1/1997 | Orth et al. |
| 5,591,224 A | 1/1997 | Schwartz et al. |
| 5,593,417 A | 1/1997 | Rhodes |
| 5,593,442 A | 1/1997 | Klein |
| 5,603,721 A | 2/1997 | Lau et al. |
| 5,609,606 A | 3/1997 | O'Boyle |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,649,952 A | 7/1997 | Lam |
| 5,651,174 A | 7/1997 | Schwartz et al. |
| 5,653,747 A | 8/1997 | Dereume |
| 5,670,161 A | 9/1997 | Healy et al. |
| 5,674,242 A | 10/1997 | Phan et al. |
| 5,674,277 A | 10/1997 | Freitag |
| 5,693,085 A | 12/1997 | Buirge et al. |
| 5,695,516 A | 12/1997 | Fischell et al. |
| 5,697,971 A | 12/1997 | Fischell et al. |
| 5,700,285 A | 12/1997 | Myers et al. |
| 5,707,386 A | 1/1998 | Schnepp-Pesch et al. |
| 5,707,388 A | 1/1998 | Lauterjung |
| 5,709,703 A | 1/1998 | Lukic et al. |
| 5,709,713 A | 1/1998 | Evans et al. |
| 5,716,393 A | 2/1998 | Lindenburg et al. |
| 5,723,003 A | 3/1998 | Winston et al. |
| 5,723,004 A | 3/1998 | Dereume et al. |
| 5,728,158 A | 3/1998 | Lau et al. |
| 5,733,303 A | 3/1998 | Israel et al. |
| 5,735,892 A | 4/1998 | Myers et al. |
| 5,735,893 A | 4/1998 | Lau et al. |
| 5,735,897 A | 4/1998 | Buirge |
| 5,738,817 A | 4/1998 | Danforth et al. |
| 5,741,325 A | 4/1998 | Chaikof et al. |
| 5,741,327 A | 4/1998 | Frantzen |
| 5,743,874 A | 4/1998 | Fischell et al. |
| 5,749,880 A | 5/1998 | Banas et al. |
| 5,755,771 A | 5/1998 | Penn et al. |
| 5,755,772 A | 5/1998 | Evans et al. |
| 5,755,774 A | 5/1998 | Pinchuk |
| 5,755,781 A | 5/1998 | Jayaraman |
| 5,769,884 A | 6/1998 | Solovay |
| 5,776,161 A | 7/1998 | Globerman |
| 5,776,181 A | 7/1998 | Lee et al. |
| 5,776,183 A | 7/1998 | Kanesaka et al. |
| 5,782,904 A | 7/1998 | White et al. |
| 5,800,526 A | 9/1998 | Anderson et al. |
| 5,807,404 A | 9/1998 | Richter |
| 5,810,868 A | 9/1998 | Lashinski et al. |
| 5,810,870 A | 9/1998 | Myers et al. |
| 5,810,872 A | 9/1998 | Kanesaka et al. |
| 5,814,063 A | 9/1998 | Freitag |
| 5,817,126 A | 10/1998 | Imran |
| 5,824,037 A | 10/1998 | Fogarty et al. |
| 5,824,045 A | 10/1998 | Alt |
| 5,824,048 A | 10/1998 | Tuch |
| 5,824,054 A | 10/1998 | Khosravi et al. |
| 5,824,059 A | 10/1998 | Wijay |
| 5,827,321 A | 10/1998 | Roubin et al. |
| 5,836,964 A | 11/1998 | Richter et al. |
| 5,836,966 A | 11/1998 | St. Germain |
| 5,843,120 A | 12/1998 | Israel et al. |
| 5,843,158 A | 12/1998 | Lenker et al. |
| 5,843,161 A | 12/1998 | Solovay |
| 5,843,164 A | 12/1998 | Frantzen et al. |
| 5,846,247 A | 12/1998 | Unsworth et al. |
| 5,853,419 A | 12/1998 | Imran |
| 5,855,598 A | 1/1999 | Pinchuk |
| 5,855,600 A | 1/1999 | Alt |
| 5,860,999 A | 1/1999 | Schnepp-Pesch et al. |
| 5,861,027 A | 1/1999 | Trapp |
| 5,868,781 A | 2/1999 | Killion |
| 5,871,538 A | 2/1999 | Dereume |
| 5,876,449 A | 3/1999 | Starck et al. |
| 5,876,450 A | 3/1999 | Johlin, Jr. |
| 5,895,406 A | 4/1999 | Gray et al. |
| 5,897,589 A | 4/1999 | Cottenceau et al. |
| 5,922,021 A | 7/1999 | Jang |
| 5,928,248 A | 7/1999 | Acker |
| 5,938,682 A | 8/1999 | Hojeibane et al. |
| 5,948,018 A | 9/1999 | Dereume et al. |
| 5,954,743 A | 9/1999 | Jang |
| 5,968,091 A | 10/1999 | Pinchuk et al. |
| 5,968,561 A | 10/1999 | Batchelder et al. |
| 5,980,552 A | 11/1999 | Pinchasik et al. |
| 5,984,965 A | 11/1999 | Knapp et al. |
| 6,017,365 A | 1/2000 | Von Oepen |
| 6,019,789 A | 2/2000 | Dinh et al. |
| 6,027,526 A | 2/2000 | Limon et al. |
| 6,033,433 A | 3/2000 | Ehr et al. |
| 6,033,434 A | 3/2000 | Borghi |
| 6,033,435 A | 3/2000 | Penn et al. |
| 6,039,756 A | 3/2000 | Jang |
| 6,048,361 A | 4/2000 | Von Oepen |
| 6,059,811 A | 5/2000 | Pinchasik et al. |
| 6,068,656 A | 5/2000 | Von Oepen |
| 6,071,308 A | 6/2000 | Ballou et al. |
| 6,086,610 A | 7/2000 | Duerig et al. |
| 6,099,561 A | 8/2000 | Alt |
| 6,106,548 A | 8/2000 | Roubin et al. |
| 6,113,627 A | 9/2000 | Jang |
| 6,117,165 A | 9/2000 | Becker |
| 6,117,535 A | 9/2000 | Szycher et al. |
| 6,123,721 A | 9/2000 | Jang |
| 6,132,460 A | 10/2000 | Thompson |
| 6,152,957 A | 11/2000 | Jang |
| 6,165,212 A | 12/2000 | Dereume et al. |
| 6,168,409 B1 | 1/2001 | Fare |
| 6,174,326 B1 | 1/2001 | Kitaoka et al. |
| 6,179,868 B1 | 1/2001 | Burpee et al. |
| 6,190,403 B1 | 2/2001 | Fischell et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,335 B1 | 3/2001 | Igaki |
| 6,203,569 B1 | 3/2001 | Wijay |
| 6,231,598 B1 | 5/2001 | Berry et al. |
| 6,231,600 B1 | 5/2001 | Zhong |
| 6,241,762 B1 | 6/2001 | Shanley |
| 6,245,101 B1 | 6/2001 | Drasler et al. |
| 6,253,443 B1 | 7/2001 | Johnson |
| 6,258,116 B1 | 7/2001 | Hojeibane |
| 6,261,318 B1 | 7/2001 | Lee et al. |
| 6,264,688 B1 | 7/2001 | Herklotz et al. |
| 6,264,690 B1 | 7/2001 | Von Oepen |
| 6,270,524 B1 | 8/2001 | Kim |
| 6,273,913 B1 | 8/2001 | Wright et al. |
| 6,299,604 B1 | 10/2001 | Ragheb et al. |
| 6,299,635 B1 | 10/2001 | Frantzen |
| 6,325,825 B1 | 12/2001 | Kula et al. |
| 6,331,189 B1 | 12/2001 | Wolinsky et al. |
| 6,332,089 B1 | 12/2001 | Acker et al. |
| 6,340,366 B2 | 1/2002 | Wijay |
| 6,348,065 B1 | 2/2002 | Brown et al. |
| 6,377,835 B1 | 4/2002 | Schoenberg et al. |
| 6,395,020 B1 | 5/2002 | Ley et al. |

| | | |
|---|---|---|
| 6,416,539 B1 | 7/2002 | Hassdenteufel |
| 6,436,132 B1 | 8/2002 | Patel et al. |
| 6,443,982 B1 | 9/2002 | Israel et al. |
| 6,451,049 B2 | 9/2002 | Vallana et al. |
| 6,485,508 B1 | 11/2002 | McGuinness |
| 6,488,702 B1 | 12/2002 | Besselink |
| 6,491,718 B1 | 12/2002 | Ahmad |
| 6,503,272 B2 | 1/2003 | Duerig et al. |
| 6,506,211 B1 | 1/2003 | Skubitz et al. |
| 6,508,834 B1 | 1/2003 | Pinchasik et al. |
| 6,540,776 B2 | 4/2003 | Sanders Millare et al. |
| 6,558,415 B2 | 5/2003 | Thompson |
| 6,572,646 B1 | 6/2003 | Boylan et al. |
| 6,589,276 B2 | 7/2003 | Pinchasik et al. |
| 6,602,285 B1 | 8/2003 | Von Oepen et al. |
| 6,607,554 B2 | 8/2003 | Dang et al. |
| 6,616,689 B1 | 9/2003 | Ainsworth et al. |
| 6,624,097 B2 | 9/2003 | Martin et al. |
| D481,139 S | 10/2003 | Seibold et al. |
| 6,629,994 B2 | 10/2003 | Gomez et al. |
| 6,652,574 B1 | 11/2003 | Jayaraman |
| 6,679,911 B2 | 1/2004 | Burgermeister |
| 6,682,554 B2 | 1/2004 | Oepen et al. |
| 6,723,119 B2 | 4/2004 | Pinchasik et al. |
| 6,730,252 B1 | 5/2004 | Teoh et al. |
| 6,740,114 B2 | 5/2004 | Burgermeister |
| 6,749,629 B1 | 6/2004 | Hong et al. |
| 6,755,856 B2 | 6/2004 | Fierens et al. |
| 6,761,733 B2 | 7/2004 | Chobotov et al. |
| 6,770,088 B2 | 8/2004 | Jang |
| 6,776,794 B1 | 8/2004 | Hong et al. |
| 6,786,922 B2 | 9/2004 | Schaeffer |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 | 4/2005 | Pinchasik et al. |
| 6,881,222 B2 | 4/2005 | White et al. |
| 6,913,619 B2 | 7/2005 | Brown et al. |
| 6,916,336 B2 | 7/2005 | Patel et al. |
| 6,929,660 B1 | 8/2005 | Ainsworth et al. |
| 6,942,689 B2 | 9/2005 | Majercak |
| 6,955,686 B2 | 10/2005 | Majercak et al. |
| 6,998,060 B2 | 2/2006 | Tomonto |
| 7,029,493 B2 | 4/2006 | Majercak et al. |
| 7,060,093 B2 | 6/2006 | Dang et al. |
| 7,128,756 B2 | 10/2006 | Lowe et al. |
| 7,141,062 B1 | 11/2006 | Pinchasik et al. |
| 7,179,286 B2 | 2/2007 | Lenz |
| 7,329,277 B2 | 2/2008 | Addonizio et al. |
| 7,520,892 B1 | 4/2009 | Ainsworth et al. |
| 7,611,531 B2 | 11/2009 | Calisse |
| 7,625,398 B2 | 12/2009 | Clifford et al. |
| 7,686,843 B2 | 3/2010 | Moore |
| 7,766,956 B2 | 8/2010 | Jang |
| 7,789,904 B2 | 9/2010 | Von Oepen et al. |
| 7,789,905 B2 | 9/2010 | Oepen et al. |
| 7,794,491 B2 | 9/2010 | Oepen et al. |
| 7,811,314 B2 | 10/2010 | Fierens et al. |
| 7,815,672 B2 | 10/2010 | Von Oepen et al. |
| 7,815,763 B2 | 10/2010 | Fierens et al. |
| 7,842,078 B2 | 11/2010 | Von Oepen et al. |
| 7,842,079 B2 | 11/2010 | Von Oepen et al. |
| 7,846,196 B2 | 12/2010 | Von Oepen et al. |
| 7,850,726 B2 | 12/2010 | Casey |
| 7,887,577 B2 | 2/2011 | Von Oepen et al. |
| 7,887,578 B2 | 2/2011 | Schneider |
| 2001/0007955 A1 | 7/2001 | Drasler et al. |
| 2001/0027339 A1 | 10/2001 | Boatman et al. |
| 2001/0049549 A1 | 12/2001 | Boylan et al. |
| 2002/0019660 A1 | 2/2002 | Gianotti et al. |
| 2002/0065549 A1 | 5/2002 | White et al. |
| 2002/0107560 A1 | 8/2002 | Richter |
| 2002/0111669 A1 | 8/2002 | Pazienza et al. |
| 2002/0113331 A1 | 8/2002 | Zhang et al. |
| 2002/0151964 A1 | 10/2002 | Smith et al. |
| 2002/0169499 A1 | 11/2002 | Zilla et al. |
| 2003/0055487 A1 | 3/2003 | Calisse |
| 2003/0083736 A1 | 5/2003 | Brown et al. |
| 2003/0114918 A1 | 6/2003 | Garrison et al. |
| 2003/0120334 A1 | 6/2003 | Gerbeding |
| 2004/0051201 A1 | 3/2004 | Greenhalgh et al. |
| 2004/0093073 A1 | 5/2004 | Lowe et al. |
| 2004/0102836 A1 | 5/2004 | Fischell et al. |
| 2004/0126405 A1 | 7/2004 | Sahatjian et al. |
| 2004/0230293 A1 | 11/2004 | Yip et al. |
| 2004/0236407 A1 | 11/2004 | Fierens et al. |
| 2004/0243220 A1 | 12/2004 | Gianotti et al. |
| 2004/0267353 A1 | 12/2004 | Gregorich |
| 2005/0075716 A1 | 4/2005 | Yan |
| 2005/0222671 A1 | 10/2005 | Schaeffer et al. |
| 2006/0015173 A1 | 1/2006 | Clifford et al. |
| 2006/0106452 A1 | 5/2006 | Niermann |
| 2006/0142844 A1 | 6/2006 | Lowe et al. |
| 2006/0184232 A1 | 8/2006 | Gianotti et al. |
| 2006/0206195 A1 | 9/2006 | Calisse |
| 2006/0247759 A1 | 11/2006 | Burpee et al. |
| 2007/0021827 A1 | 1/2007 | Lowe et al. |
| 2007/0021834 A1 | 1/2007 | Young et al. |
| 2007/0179593 A1 | 8/2007 | Fierens et al. |
| 2007/0213800 A1 | 9/2007 | Fierens et al. |
| 2007/0299505 A1 | 12/2007 | Gregorich et al. |
| 2008/0077231 A1 | 3/2008 | Heringes et al. |
| 2008/0294239 A1 | 11/2008 | Casey |
| 2008/0294240 A1 | 11/2008 | Casey |
| 2009/0163992 A1 | 6/2009 | Osman et al. |
| 2009/0163996 A1 | 6/2009 | Bregulla |
| 2009/0163998 A1 | 6/2009 | Casey |
| 2010/0114297 A1 | 5/2010 | Calisse |
| 2011/0004289 A1 | 1/2011 | Von Oepen et al. |
| 2011/0022159 A1 | 1/2011 | Fierens et al. |
| 2012/0165921 A1 | 6/2012 | Casey |

FOREIGN PATENT DOCUMENTS

| | | |
|---|---|---|
| EP | 0357003 | 3/1990 |
| EP | 0221570 | 1/1991 |
| EP | 0699451 | 3/1996 |
| EP | 0709067 | 5/1996 |
| EP | 0808614 | 11/1997 |
| EP | 0815806 | 1/1998 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7-24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO96/21404 | 7/1996 |
| WO | WO96/25124 | 8/1996 |
| WO | WO97/12563 | 4/1997 |
| WO | WO97/12564 | 4/1997 |
| WO | WO97/14375 | 4/1997 |
| WO | WO98/32412 | 7/1998 |
| WO | WO98/47447 | 10/1998 |
| WO | WO99/07308 | 2/1999 |
| WO | WO99/17680 | 4/1999 |
| WO | WO99/23976 | 5/1999 |
| WO | WO99/38456 | 8/1999 |
| WO | WO99/38458 | 8/1999 |
| WO | WO99/39660 | 8/1999 |
| WO | WO99/39663 | 8/1999 |
| WO | WO99/49928 | 10/1999 |
| WO | WO00/13611 | 3/2000 |
| WO | WO00/32241 | 6/2000 |
| WO | WO00/45744 | 8/2000 |
| WO | WO00/53119 | 9/2000 |
| WO | WO01/01885 | 1/2001 |
| WO | WO01/82835 | 11/2001 |
| WO | WO02/026164 | 4/2002 |
| WO | WO02/064061 | 8/2002 |

| | | |
|---|---|---|
| WO | WO02/064065 | 8/2002 |
| WO | WO02/094127 | 11/2002 |
| WO | WO03/009779 | 2/2003 |
| WO | WO03/057076 | 7/2003 |
| WO | WO2004/087015 | 10/2004 |
| WO | WO2006/055533 | 5/2006 |
| WO | WO2006/066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |
| WO | WO2009/080326 | 7/2009 |
| WO | WO2009/080327 | 7/2009 |

OTHER PUBLICATIONS

U.S. Appl. No. 11/731,820, mail date Mar. 30, 2011, Issue Notification.
U.S. Appl. No. 11/973,707, mail date Oct. 12, 2011, Notice of Allowance.
U.S. Appl. No. 12/966,916, mail date Jan. 5, 2012, Office Action.
U.S. Appl. No. 11/731,882, mail date Aug. 29, 2011, Notice of Allowance.
U.S. Appl. No. 11/805,584, mail date Aug. 24, 2011, Issue Notification.
U.S. Appl. No. 11/404,450, mail date Aug. 10, 2011, Office Action.
U.S. Appl. No. 12/895,032, mail date Feb. 1, 2012, Office Action.
U.S. Appl. No. 11/404,450, mail date Jan. 31, 2012, Office Action.
U.S. Appl. No. 11/805,584, mail date May 12, 2011, Notice of Allowance.
U.S. Appl. No. 13/089,039, filed Apr. 8, 2011, Fierens et al.
U.S. Appl. No. 60/637,495, filed Dec. 20, 2004, Fierens et al.
U.S. Appl. No. 12/966,916, filed Dec. 13, 2010, Casey.
U.S. Appl. No. 09/582,318, mail date Aug. 14, 2002, Office Action.
U.S. Appl. No. 09/582,318, mail date Mar. 7, 2003, Notice of Allowance.
U.S. Appl. No. 09/742,144, mail date Sep. 24, 2002, Office Action.
U.S. Appl. No. 09/742,144, mail date May 14, 2003, Office Action.
U.S. Appl. No. 09/742,144, mail date Aug. 29, 2003, Notice of Allowance.
U.S. Appl. No. 09/916,394, mail date Aug. 12, 2003, Office action.
U.S. Appl. No. 09/916,394, mail date Oct. 9, 2003, Office action.
U.S. Appl. No. 09/916,394, mail date Mar. 2, 2004, Office action.
U.S. Appl. No. 09/967,789, mail date Sep. 17, 2003, Office Action.
U.S. Appl. No. 09/967,789, mail date Feb. 17, 2004, Notice of Allowance.
U.S. Appl. No. 10/241,523, mail date Aug. 18, 2004, Office Action.
U.S. Appl. No. 10/241,523, mail date Oct. 25, 2004, Office Action.
U.S. Appl. No. 10/241,523, mail date Mar. 8, 2005, Office Action.
U.S. Appl. No. 10/241,523, mail date Jun. 3, 2005, Office Action.
U.S. Appl. No. 10/241,523, mail date Aug. 23, 2005, Office Action.
U.S. Appl. No. 10/241,523, mail date Nov. 16, 2005, Office Action.
U.S. Appl. No. 10/241,523, mail date Apr. 27, 2006, Office Action.
U.S. Appl. No. 10/743,857, mail date Mar. 15, 2007, Office Action.
U.S. Appl. No. 10/743,857, mail date Nov. 16, 2007, Office Action.
U.S. Appl. No. 10/743,857, mail date May 8, 2008, Office Action.
U.S. Appl. No. 10/743,857, mail date Jan. 6, 2009, Office Action.
U.S. Appl. No. 10/743,857, mail date May 27, 2009, Office Action.
U.S. Appl. No. 10/743,857, mail date Feb. 12, 2010, Notice of Allowance.
U.S. Appl. No. 10/743,857, mail date Jun. 25, 2010, Notice of Allowance.
U.S. Appl. No. 10/743,857, mail date Aug. 18, 2010, Issue Notification.
U.S. Appl. No. 10/859,636, mail date Jun. 1, 2007, Office action.
U.S. Appl. No. 10/859,636, mail date Dec. 31, 2007, Office action.
U.S. Appl. No. 10/859,636, mail date Apr. 15, 2008, Office Action.
U.S. Appl. No. 10/859,636, mail date Oct. 1, 2008, Notice of Allowance.
U.S. Appl. No. 10/859,636, mail date Mar. 5, 2009, Office Action.
U.S. Appl. No. 10/859,636, mail date Oct. 19, 2009, Notice of Allowance.
U.S. Appl. No. 10/859,636, mail date Feb. 1, 2010, Notice of Allowance.
U.S. Appl. No. 10/859,636, mail date May 19, 2010, Notice of Allowance.
U.S. Appl. No. 10/859,636, mail date Dec. 9, 2010, Notice of Allowance.
U.S. Appl. No. 10/884,613, mail date Mar. 30, 2005, Office action.
U.S. Appl. No. 10/884,613, mail date Nov. 14, 2005, Office action.
U.S. Appl. No. 10/903,013, mail date Mar. 15, 2007, Office Action.
U.S. Appl. No. 10/903,013, mail date Nov. 19, 2007, Office Action.
U.S. Appl. No. 10/903,013, mail date May 14, 2008, Office Action.
U.S. Appl. No. 10/903,013, mail date Jan. 5, 2009, Office Action.
U.S. Appl. No. 10/903,013, mail date May 27, 2009, Office Action.
U.S. Appl. No. 10/903,013, mail date Feb. 12, 2010, Notice of Allowance.
U.S. Appl. No. 10/903,013, mail date Jun. 24, 2010, Notice of Allowance.
U.S. Appl. No. 10/903,013, mail date Aug. 18, 2010, Issue Notification.
U.S. Appl. No. 10/903,014, mail date Mar. 15, 2007, Office Action.
U.S. Appl. No. 10/903,014, mail date Nov. 16, 2007, Office Action.
U.S. Appl. No. 10/903,014, mail date May 13, 2008, Office Action.
U.S. Appl. No. 10/903,014, mail date Jan. 13, 2009, Office Action.
U.S. Appl. No. 10/903,014, mail date Jun. 1, 2009, Office Action.
U.S. Appl. No. 10/903,014, mail date Feb. 5, 2010, Notice of Allowance.
U.S. Appl. No. 10/903,014, mail date May 26, 2010, Office Action.
U.S. Appl. No. 10/903,014, mail date Jun. 24, 2010, Notice of Allowance.
U.S. Appl. No. 10/903,014, mail date Aug. 25, 2010, Issue Notification.
U.S. Appl. No. 10/903,080, mail date Mar. 15, 2007, Office Action.
U.S. Appl. No. 10/903,080, mail date Nov. 19, 2007, Office Action.
U.S. Appl. No. 10/903,080, mail date May 12, 2008, Office Action.
U.S. Appl. No. 10/903,080, mail date Dec. 30, 2008, Office Action.
U.S. Appl. No. 10/903,080, mail date May 27, 2009, Office Action.
U.S. Appl. No. 10/903,080, mail date Jan. 13, 2010, Notice of Allowance.
U.S. Appl. No. 10/903,080, mail date Sep. 16, 2010, Notice of Allowance.
U.S. Appl. No. 10/909,117, mail date Aug. 22, 2007, Office Action.
U.S. Appl. No. 10/909,117, mail date May 12, 2008, Office Action.
U.S. Appl. No. 10/909,117, mail date Dec. 30, 2008, Office Action.
U.S. Appl. No. 10/909,117, mail date May 27, 2009, Office Action.
U.S. Appl. No. 10/909,117, mail date Jan. 13, 2010, Notice of Allowance.
U.S. Appl. No. 10/909,117, mail date Sep. 16, 2010, Notice of Allowance.
U.S. Appl. No. 10/909,117, mail date Nov. 17, 2010, Issue Notification.
U.S. Appl. No. 10/909,118, mail date Mar. 29, 2007, Office Action.
U.S. Appl. No. 10/909,118, mail date Nov. 19, 2007, Office Action.
U.S. Appl. No. 10/909,118, mail date May 12, 2008, Office Action.
U.S. Appl. No. 10/909,118, mail date Jan. 5, 2009, Office Action.
U.S. Appl. No. 10/909,118, mail date Jul. 24, 2009, Office Action.
U.S. Appl. No. 10/909,118, mail date Jan. 13, 2010, Notice of Allowance.
U.S. Appl. No. 10/909,118, mail date Sep. 21, 2010, Notice of Allowance.
U.S. Appl. No. 10/954,948, mail date Mar. 15, 2007, Office Action.
U.S. Appl. No. 10/954,948, mail date Nov. 16, 2007, Office Action.
U.S. Appl. No. 10/954,948, mail date May 15, 2008, Office Action.
U.S. Appl. No. 10/954,948, mail date Jan. 13, 2009, Office Action.
U.S. Appl. No. 10/954,948, mail date May 29, 2009, Office Action.
U.S. Appl. No. 10/954,948, mail date Jan. 13, 2010, Notice of Allowance.
U.S. Appl. No. 10/954,948, mail date Jul. 6, 2010, Notice of Allowance.
U.S. Appl. No. 10/955,425, mail date Mar. 15, 2007, Office Action.
U.S. Appl. No. 10/955,425, mail date Nov. 16, 2007, Office Action.
U.S. Appl. No. 10/955,425, mail date May 13, 2008, Office Action.
U.S. Appl. No. 10/955,425, mail date Jan. 13, 2009, Office Action.
U.S. Appl. No. 10/955,425, mail date May 28, 2009, Office Action.
U.S. Appl. No. 10/955,425, mail date Feb. 26, 2010, Notice of Allowance.

U.S. Appl. No. 10/955,425, mail date Jun. 25, 2010, Notice of Allowance.
U.S. Appl. No. 10/955,425, mail date Sep. 30, 2010, Issue Notification.
U.S. Appl. No. 11/313,110, mail date Jan. 8, 2008, Office Action.
U.S. Appl. No. 11/313,110, mail date Jul. 2, 2008, Office Action.
U.S. Appl. No. 11/313,110, mail date Mar. 3, 2009, Office Action.
U.S. Appl. No. 11/313,110, mail date Nov. 2, 2009, Notice of Allowance.
U.S. Appl. No. 11/313,110, mail date Feb. 18, 2010, Notice of Allowance.
U.S. Appl. No. 11/313,110, mail date Jun. 15, 2010, Notice of Allowance.
U.S. Appl. No. 11/313,110, mail date Sep. 29, 2010, Issue Notification.
U.S. Appl. No. 11/404,450, mail date Feb. 4, 2009, Office Action.
U.S. Appl. No. 11/404,450, mail date Mar. 17, 2009, Office Action.
U.S. Appl. No. 11/404,450, mail date Sep. 30, 2009, Office Action.
U.S. Appl. No. 11/404,450, mail date Apr. 22, 2010, Office Action.
U.S. Appl. No. 11/404,450, mail date Nov. 26, 2010, Office Action.
U.S. Appl. No. 11/435,260, mail date Jan. 10, 2008, Office Action.
U.S. Appl. No. 11/435,260, mail date Mar. 26, 2008, Office Action.
U.S. Appl. No. 11/435,260, mail date Dec. 16, 2008, Office Action.
U.S. Appl. No. 11/435,260, mail date Jun. 18, 2009, Notice of Allowance.
U.S. Appl. No. 11/435,260, mail date Jun. 26, 2009, Notice of Allowance.
U.S. Appl. No. 11/601,475, mail date Jul. 22, 2008, Office Action.
U.S. Appl. No. 11/601,475, mail date Jan. 6, 2009, Office Action.
U.S. Appl. No. 11/601,475, mail date Jun. 1, 2009, Office Action.
U.S. Appl. No. 11/601,475, mail date Jan. 15, 2010, Notice of Allowance.
U.S. Appl. No. 11/601,475, mail date Jul. 9, 2010, Notice of Allowance.
U.S. Appl. No. 11/731,820, mail date Jan. 27, 2010, Office Action.
U.S. Appl. No. 11/731,820, mail date Aug. 5, 2010, Notice of Allowance.
U.S. Appl. No. 11/731,820, mail date Dec. 16, 2010, Notice of Allowance.
U.S. Appl. No. 11/731,882, mail date Feb. 3, 2010, Office Action.
U.S. Appl. No. 11/731,882, mail date Sep. 1, 2010, Office Action.
U.S. Appl. No. 11/732,244, mail date Sep. 28, 2009, Office Action.
U.S. Appl. No. 11/732,244, mail date May 5, 2010, Notice of Allowance.
U.S. Appl. No. 11/732,244, mail date Jun. 21, 2010, Notice of Allowance.
U.S. Appl. No. 11/732,244, mail date Sep. 22, 2010, Issue Notification.
U.S. Appl. No. 11/805,584, mail date Apr. 27, 2009, Office Action.
U.S. Appl. No. 11/805,584, mail date Oct. 29, 2009, Office Action.
U.S. Appl. No. 11/805,584, mail date Mar. 15, 2010, Office Action.
U.S. Appl. No. 11/805,584, mail date Oct. 4, 2010, Office Action.
U.S. Appl. No. 11/961,290, mail date May 6, 2009, Office Action.
U.S. Appl. No. 11/961,290, mail date Dec. 18, 2009, Office Action.
U.S. Appl. No. 11/961,384, mail date May 26, 2009, Office Action.
U.S. Appl. No. 11/961,384, mail date Oct. 8, 2009, Office Action.
U.S. Appl. No. 11/961,754, mail date Jul. 22, 2009, Office Action.
U.S. Appl. No. 11/961,754, mail date Apr. 5, 2010, Notice of Allowance.
U.S. Appl. No. 11/961,754, mail date Jul. 28, 2010, Notice of Allowance.
U.S. Appl. No. 11/961,754, mail date Nov. 23, 2010, Issue Notification.
U.S. Appl. No. 11/973,707, mail date Jun. 9, 2009, Office Action.
U.S. Appl. No. 11/973,707, mail date Mar. 19, 2010, Office Action.
U.S. Appl. No. 11/961,775, mail date Oct. 1, 2009, Office Action.
U.S. Appl. No. 11/961,775, mail date Mar. 31, 2010, Office Action.
U.S. Appl. No. 12/966,916, mail date Jun. 10, 2011, Office Action.
Landers, Rüdiger and Mülhaupt, Rolf "Desktop manufacturing of complex objects, prototypes and biomedical scaffolds by means of computer-assisted design combined with computer-guided 3D plotting of polymers and reactive oligomers" Macromolecular Materials and Engineering , vol. 282, Issue 1, pp. 17-21, Oct. 2000.
U.S. Appl. No. 12/608,335, mail date May 11, 2012, Office Action.
U.S. Appl. No. 12/966,916, mail date May 23, 2012, Notice of Allowance.
U.S. Appl. No. 11/961,384, mail date Apr. 23, 2012, Office Action.
U.S. Appl. No. 12/875,971, mail date Apr. 19, 2012, Restriction Requirement.
U.S. Appl. No. 12/895,032, mail date Jul. 3, 2012, Office Action.
U.S. Appl. No. 11/961,290, filed Aug. 3, 2012, Office Action.
U.S. Appl. No. 12/875,971, filed Jul. 26, 2012, Notice of Allowance.
U.S. Appl. No. 12/966,916, filed Aug. 1, 2012, Issue Notification.
U.S. Appl. No. 11/961,384, filed Aug. 21, 2012, Notice of Allowance.

STENT HAVING AN EXPANDABLE WEB STRUCTURE

RELATED APPLICATIONS

The present application is a continuation application of U.S. patent application Ser. No. 11/601,475, filed on Nov. 16, 2006, now U.S. Pat. No. 7,887,578.

FIELD OF THE INVENTION

The present invention relates to stents. More particularly, the present invention relates to stents having a web structure that minimizes stent non-uniformity during crimping and subsequent expansion of the stent.

BACKGROUND OF THE INVENTION

Stents are tubular structures that are implanted inside the lumen of a vessel or other body passageway to retain the patency of the vessel or passageway. Typically, stents are inserted into the lumen in a contracted condition and then either are expanded in situ with the aid of a catheter balloon, or expand autonomously. If an angioplasty procedure were performed without stent implantation, restenosis may occur as a result of elastic recoil of the stenotic lesion.

Various stent designs are known in the art and typically comprise a tubular body that expands from a contracted condition to a deployed condition. A common drawback of such stents is that the stent decreases in length, or foreshortens, along its longitudinal axis as it expands. Such foreshortening is undesirable because, in the deployed configuration, the stent may not span the entire area inside a vessel or orifice that requires expansion and/or support. In addition, foreshortening may result in non-uniformity of the stent in the deployed configuration.

Therefore, it would be desirable to provide a stent that has a radial stiffness in the expanded deployed configuration sufficient to maintain vessel patency in a stenosed vessel.

Further, it would be desirable to provide a stent that experiences reduced foreshortening, thereby reducing stent non-uniformity resulting from contraction and subsequent expansion.

Still further, it would be desirable to provide a stent that retains a homogenous cross-section and stress distribution after deployment.

SUMMARY OF THE INVENTION

In view of the foregoing, it is an object of the present invention to provide a stent having a radial stiffness in the expanded configuration that is sufficient to maintain vessel patency in a stenosed vessel.

It is another object of the present invention to provide a stent that experiences reduced foreshortening, thereby reducing non-uniformity resulting from contraction and subsequent expansion of the stent.

It is a further object of the present invention to provide a stent that retains a homogenous cross-section and stress distribution after deployment.

These and other objects of the present invention are accomplished by providing a stent having a tubular body and with a longitudinal wall formed by a web structure that expands from a contracted configuration to a deployed configuration. The web structure is composed of a plurality of neighboring web patterns that extend circumferentially around the longitudinal wall and that are adjoined by transition sections.

In one embodiment, each of the web patterns comprises a plurality of arcuate struts that are sequentially interconnected by bends and that are arranged in neighboring web patterns of opposing concavities. Each of the transition sections connecting neighboring web patterns is formed by adjoining two adjacent bends of opposite curvatures to generate an essentially X-shaped transition section.

Preferably, each X-shaped transition section is produced by contacting the upward end of a bend interconnecting two concave struts with the neighboring downward end of a bend interconnecting two concave struts. This arrangement causes the X-shaped transition section to be disposed at an angle relation to the longitudinal axis of the stent, thereby reducing the empty spaces between the web patterns. Also preferably, the X-shaped transition sections connect one out of every three couples of adjacent bends, and the transition sections extending from one end of a web pattern are staggered in relation to the transition sections extending from the opposite end of the same web pattern.

In one embodiment, the web structure includes a plurality of web patterns interconnected with one another at a plurality of X-shaped transition sections, and that are arranged so that the web patterns are situated side-by-side along the longitudinal length of the tubular body, with each web pattern also extending circumferentially around the wall. At least one of the interconnected web patterns includes at least three webs joined end-to-end so as to extend between a first pair of X-shaped transition sections with no intervening X-shaped transition sections between the first pair of X-shaped transition sections. A single web is connected between a second pair of X-shaped transition sections with no intervening X-shaped transition sections between the second pair of interconnection locations.

The stent according to the present embodiment may be designed to be balloon expandable or self-expanding, and may be manufactured from a variety of materials, including polymeric materials, for example poly-L-lactid materials, or metallic materials or metal alloys, for example stainless steel, titanium, platinum, tantalum, titanium alloys, platinum alloys, nickel-titanium alloys such as Nitinol, platinum-Nitinol alloys, tantalum alloys, cobalt-chromium alloys or combinations of the above mentioned materials and alloys. Additionally, the stent according to the present embodiment may be manufactured with single or multiple layer structures, for example, with a two or three layer structure.

Further, the stent according to the present embodiment may be radiopaque, in order to facilitate insertion and positioning by a clinician, and be coated with a therapeutic agent, such as an agent that retards thrombus formation or restenosis, or with a therapeutic agent that provides systemic or local delivery via the blood system.

In another embodiment of the invention, the stent has the same configuration as in the previously described embodiment, except that each of the arcuate struts includes at least one substantially straight section. Preferably, each strut is formed by three substantially straight sections that are joined to define two adjacent obtuse angles.

Therefore, the above described embodiments are distinguished by the rounded shape of the struts in the first embodiment, and by the segmented shape of the struts in the second embodiment'. In either embodiment, neighboring web patterns are coupled by the previously described X-shaped transition sections.

As will be apparent to one skilled in the art, the position, distribution density, and thickness of adjoining struts and X-shaped transition sections may be varied to provide stents with characteristics tailored to specific applications, such as implantations in coronary arteries or in peripheral arteries, for example, renal arteries. Position, distribution density, and thickness also may be varied to provide varying flexibility and radial stiffness properties along the length of an individual stent.

A stent according to the present invention minimizes stent non-uniformity during contraction and expansion of the stent, because variations in stent length and properties are reduced by the X-shaped transition sections. This beneficial effect is caused by having transition sections between adjacent web patterns that are positioned near the mid-points between web patterns.

Stents according to the present invention are longitudinally flexible in the delivery configuration, so to increase a clinician's ability to guide the stent to a target site within a patient's vessel, but are radially stiff in the deployed configuration, so to withstand the compressive forces applied by a vessel wall and maintain vessel patency. The web structure described hereinabove provides such a desirable combination of flexibility in the delivery configuration and radial stiffness in the deployed configuration.

Methods of making and using the stents of the present invention also are described.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which.

DETAILED DESCRIPTION OF THE INVENTION

The present invention is directed to stents having a web structure and that are configured to expand from a contracted delivery configuration to an expanded deployed configuration.

In accordance with the principles of the present invention, the stents are formed of a plurality of ring-shaped circumferential web patterns interconnected by X-shaped transition sections. Depending on the material of fabrication, the stents of the present invention may be expanded using a balloon catheter or be self-expanding. Further, the stents may be radiopaque, in order to facilitate delivery, and may comprise a therapeutic coating.

Figure 1:
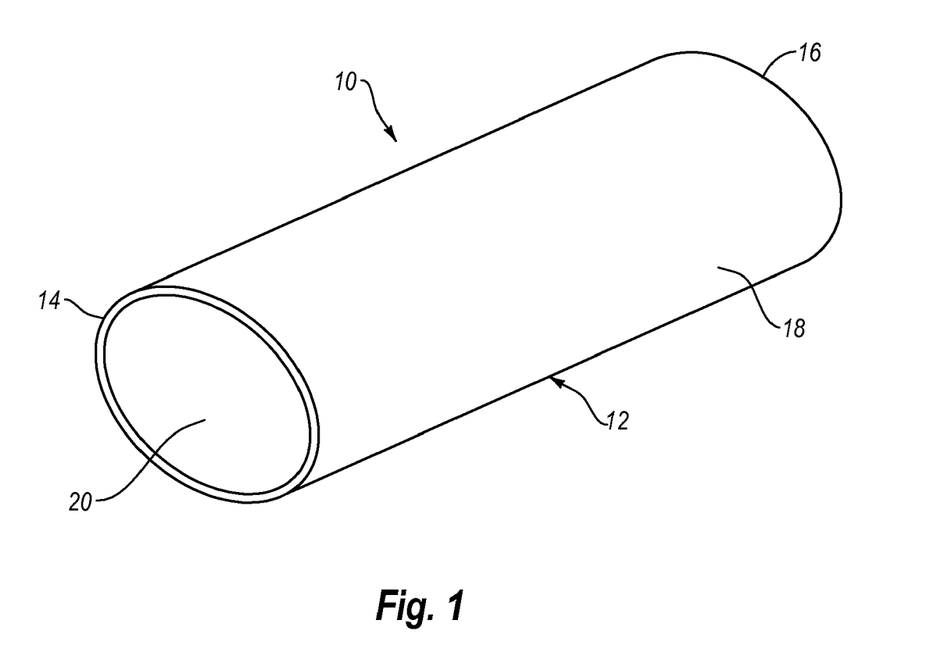
FIG. 1 is a schematic isometric view illustrating the tubular structure of a stent according to the present invention.

Referring first to FIG. 1, there is shown the general tubular shape of stent 10 that comprises flexible tubular body 12 having proximal end 14, distal end 16, and essentially cylindrical wall 18 that defines lumen 20 between proximal end 14 and distal end 16.

Figure 2A:
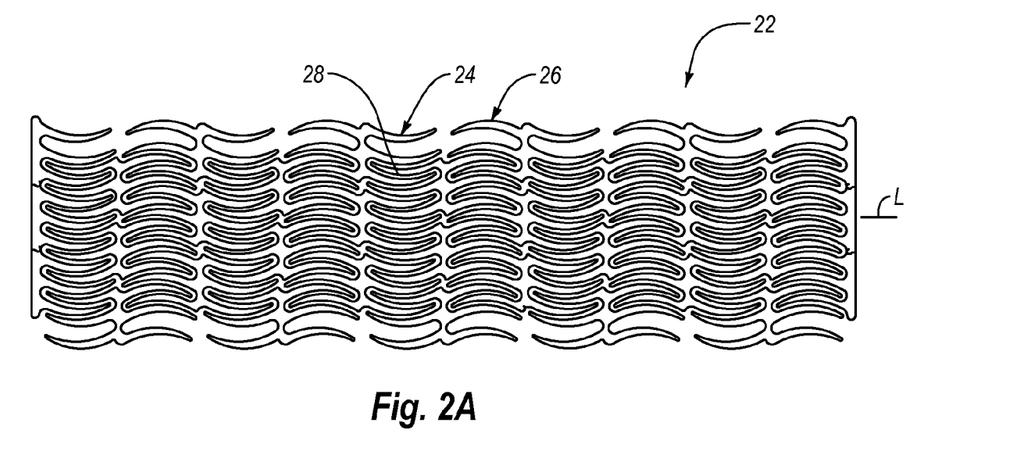
FIGS. 2A-2C are detail views illustrating the web structure of a first embodiment of the stent of FIG. 1.
Figure 2B:
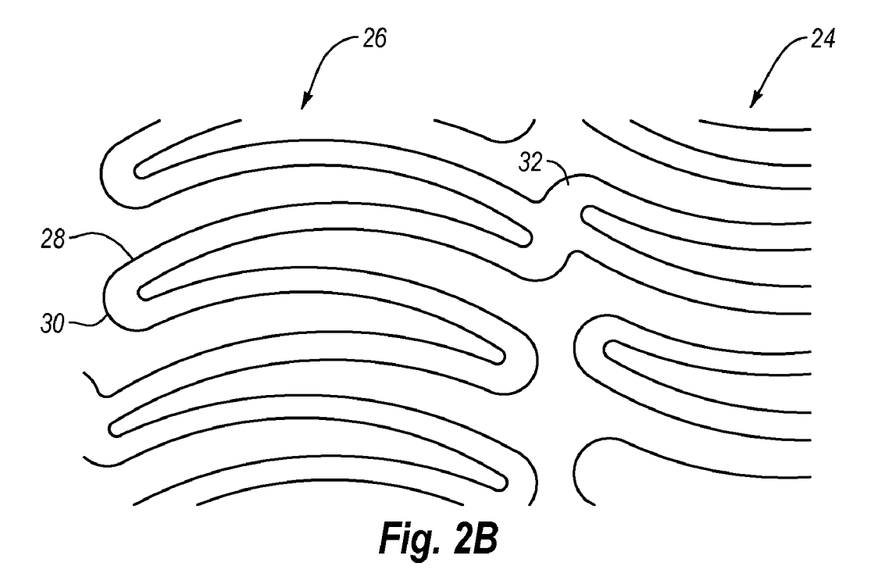
Figure 2C:
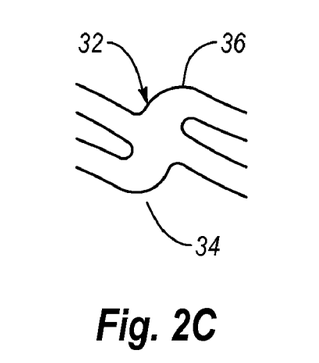

FIGS. 2A-2C represent detail views of a first embodiment of the present invention. Wall 18 is composed of web structure 22, which, for illustrative purposes, is shown flattened into a plane. More particularly, FIG. 2A illustrates the pattern and orientation of web structure 22 in relation to the longitudinal axis L of stent 10.

Web structure 22 is formed by a plurality of neighboring web patterns 24 and 26, which extend circumferentially around tubular body 12 and which are arranged side by side. Thus, web patterns 24 and 26 are arranged longitudinally in the sequence 24, 26, 24, 26, etc.

As shown in FIGS. 2A-2B, web patterns 24 and 26 each comprise a plurality of arcuate struts 28, arranged with alternating concavity relative to the circumferential of the stent. Each of arcuate struts 28 is connected sequentially to the adjoining strut inside the same web pattern by bend 30, and arcuate struts 28 are disposed in a nested arrangement to form a stack of substantially parallel curvilinear segments within each of web patterns 24 and 26.

Referring now to FIGS. 2B-2C, neighboring web patterns along longitudinal axis L are connected one to the other by a plurality of transition sections 32. Each transition section 32 is formed where a pair of adjacent bends 30 of opposite concavities meet to create what is an essentially "X"-shaped transition section.

The positions, distribution densities, and thickness of transition sections 32 may be varied to suit specific applications. For example, one skilled in the art will recognize that the angular dispositions of X-shaped transition sections 32 is determined by the specific points of contact between neighboring bends 30. FIG. 2C illustrates a preferred arrangement, wherein X-shaped transition section 32 is formed by contacting the upward end of a first bend 34, that interconnects two downward concave struts, with the neighboring downward end of bend 36, that connects two upward concave struts. However, other points of contact between neighboring bends are possible and are within the scope of the present invention.

X-shaped transition section 32 also may be positioned at different angles in relation to longitudinal axis L of tubular flexible body 12. In the embodiment illustrated in FIG. 2B, X-shaped transition section 32 is disposed at an angle of approximately 30 degrees relative to longitudinal axis L. However, different angles also are possible and also are within the scope of the present invention.

Transition sections 32 that connect neighboring web patterns 24 and 26 may vary in number and in disposition in different embodiments of the invention. FIG. 2A illustrates an embodiment, in which every third pair of adjacent bends 30 are connected by transition section 32. In the embodiment of FIG. 2A, transition sections 32 extending at opposite ends of each of web patterns 24 or 26 are staggered relative to the longitudinal axis of the stent. This arrangement causes stent 10 to assume a more uniform longitudinal shape and stress distribution than can be achieved with other configurations, in which transition sections at opposing ends of web patterns 24 and 25 are aligned. For example, this arrangement of web structure 22 enables stent 10 to retain its the expanded configuration more readily under the radial stress from the vessel wall.

Further, because transition sections 32 have a reduced length compared to previously known designs, a stent according to the present invention experiences reduced non-uniformity during crimping and subsequent expansion, as well as reduced foreshortening.

Web patterns 24 and 26 preferably are manufactured by laser-cutting a tubular member, or by a combination of laser and slit cutting of a tubular member. As previously mentioned, stent 10 may be deployed by expanding it with a balloon, or, alternatively, stent 10 may be configured to self-expand. If balloon expandable, the tubular member preferably is made of a deformable material, such as stainless steel or titanium. If self-expanding, the tubular member preferably is made of a shape memory, superelastic alloy, such as a nickel-titanium alloy.

Preferably, stent 10 is radiopaque to facilitate insertion and positioning into a vessel or organ by a clinician, who can then monitor progress during implantation with a display. Stent 10 also is preferably coated with a therapeutic agent, such as a medication that retards thrombus formation or restenosis, or with a therapeutic agent that may be delivered systemically or via the blood system.

Figure 3A:
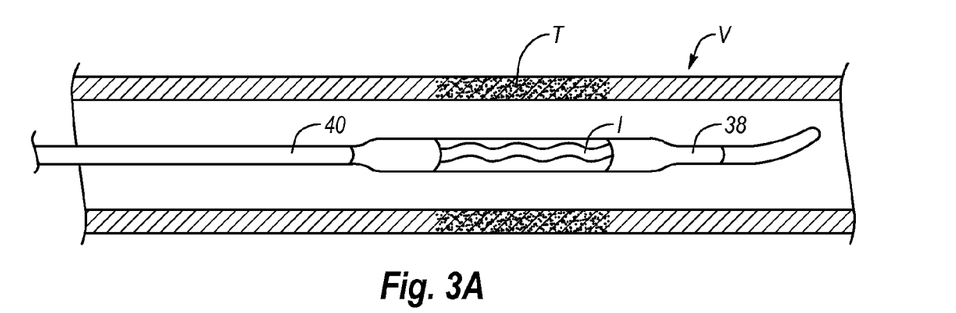
FIGS. 3A-3D show a method of deploying a balloon expandable stent constructed in accordance with the present invention.

Referring now to FIGS. 3A-3D, a method of using a balloon expandable embodiment of stent 10 is described. Stent 10 is disposed in a contracted delivery configuration over balloon 38 of balloon catheter 40. As shown in FIG. 3A, the distal end of catheter 30 is delivered to a target site T within a patient's vessel V using, for example, well-known percutaneous techniques. Target site T may, for example, comprise a stenosed region of vessel V, at which an angioplasty procedure has been conducted. Stent 10 or portions of catheter 40 preferably is radiopaque to facilitate positioning and implantation within the vessel.

Figure 3B:
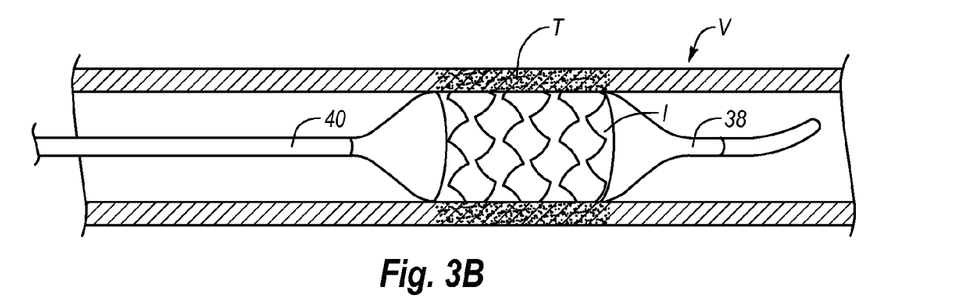
Figure 3C:
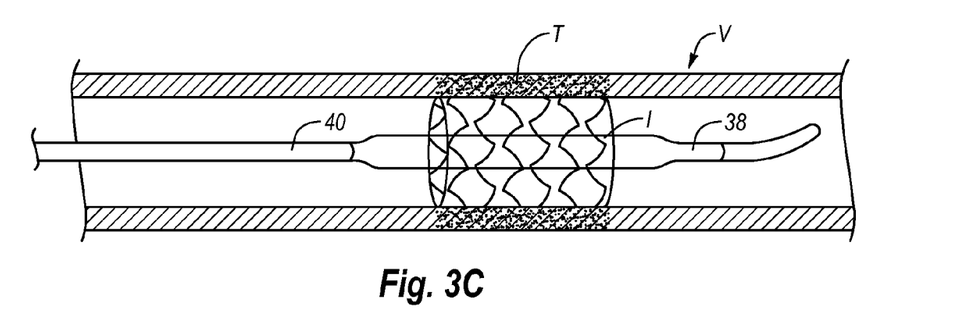
Figure 3D:
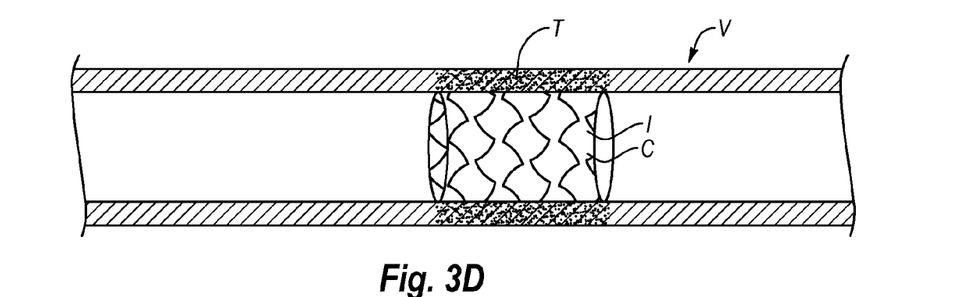

In FIG. 3B, balloon 38 is inflated to expand stent 10 to the deployed configuration, in which stent 10 contacts the wall of vessel V at target site T. Advantageously, the web pattern of stent 10 described hereinabove reduces length change during expansion, thereby ensuring that stent 10 covers all of target site T. Balloon 30 then is deflated, as seen in FIG. 3C, and balloon catheter 40 is removed from vessel V, as seen in FIG. 3D.

Stent 10 remains within the vessel, with its web structure supporting the vessel and reducing restenosis. Stent 10 also may comprise external coating C configured to retard restenosis or thrombosis formation around the stent, and coating C may alternatively deliver therapeutic agents into the patient's blood stream.

Figure 4A:
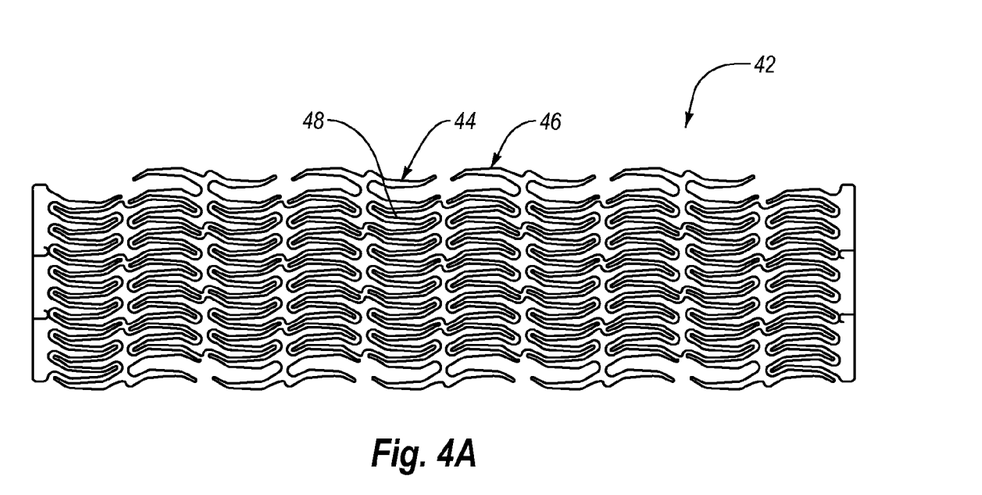
FIGS. 4A-4C are detail views illustrating a web structure of a second embodiment of the stent of FIG. 1.
Figure 4B:
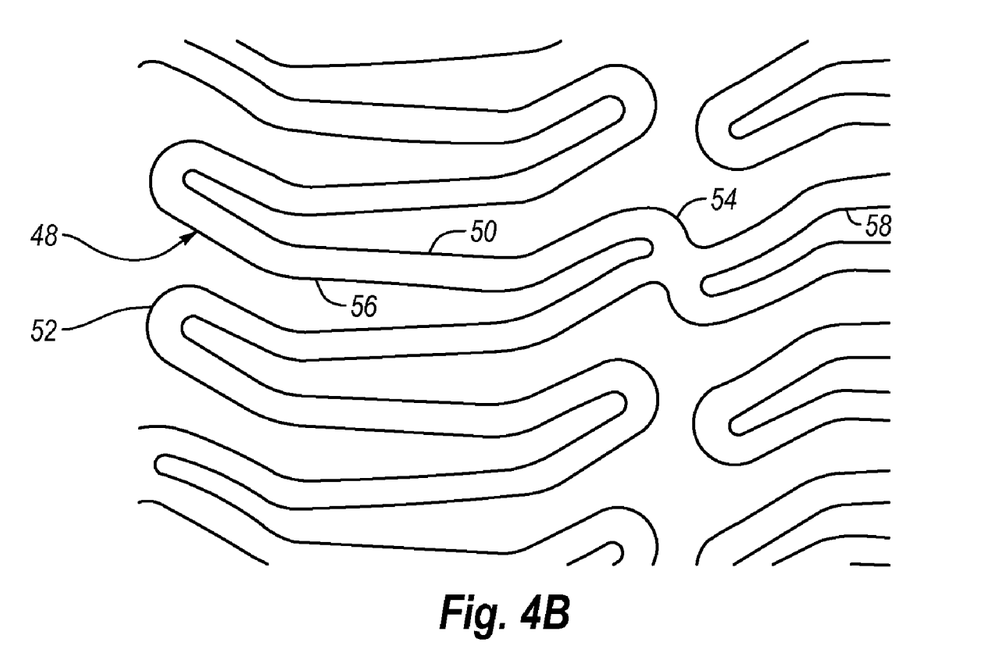
Figure 4C:
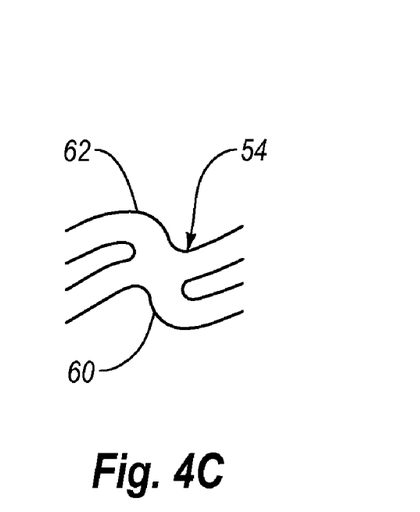

Turning now to FIGS. 4A-4C, there is shown a second embodiment of the invention. Web structure 42 is formed by a plurality of web patterns 44 and 46, which are disposed in alternating positions, in the manner shown for web patterns 24 and 26 of the embodiment of FIG. 2A. Each of web patterns 44 and 46 is formed by a plurality of struts 48, which have alternating concavities and which are parallel and nested into each other, also in the same fashion as struts 28 in FIG. 2A. As shown in FIG. 4B, each of struts 48 comprises a series of straight and curved segments, or by a series of straight segments 50 (three in the embodiment illustrated in FIG. 4B) disposed next to each other to form obtuse angles therebetween.

Adjacent struts 50 within a web pattern are sequentially connected one to the other by bend 52, and neighboring web patterns are interconnected by means of a plurality of X-shaped transition sections 54, that couple pairs of adjacent bends 52, positioned on neighboring web patterns 44 and 46, one another. When stent 10 is compressed to the contracted delivery configuration, central segments 56 and 58 preferably are substantially aligned with the longitudinal axis L of the tubular body 12, and the angles between struts 50 increase in magnitude as stent 10 expands to its deployed configuration.

The foregoing arrangement beneficially provides increased radial stiffness in the expanded configuration of stent 10. Thus, stent 10 is longitudinally flexible in the contracted delivery configuration, to facilitate delivery through a tortuous anatomy, but exhibits sufficient radial stiffness in the expanded configuration to ensure vessel patency, even when deployed in an area of stenosis. The increase in the angular of X-shaped transition sections 54 also reduces foreshortening during stent expansion, thereby decreasing the likelihood that the stent will not completely span a target site within a patient's vessel after deployment.

As in the previous embodiment, the X-shaped transition section preferably is formed by contacting the upward end of a first bend 60, that interconnects two downward concave struts, with the downward end of bend 62, that interconnects two upward concave struts in the neighboring web pattern. This arrangement provides a X-shaped transition section that has a longitudinal axis disposed at about 30 degrees from the longitudinal axis of the strut. In addition, this arrangement reduces stent non-uniformity during crimping and expansion, because transition section 54 is situated and oriented so to reduce differences in strut length. Other modes of connection between neighboring bends to form X-shaped transition section 54 also are possible and are within the scope of the present invention.

Also as in the previous embodiment, X-shaped transition sections 54 preferably connect one out of every three pairs of adjacent bends on a web pattern. Further, the transition sections extending from one end of each web pattern 24 or 26 preferably are disposed in a staggered arrangement relative to the transition ends extending from the opposite end of the same web pattern.

Figure 5A:
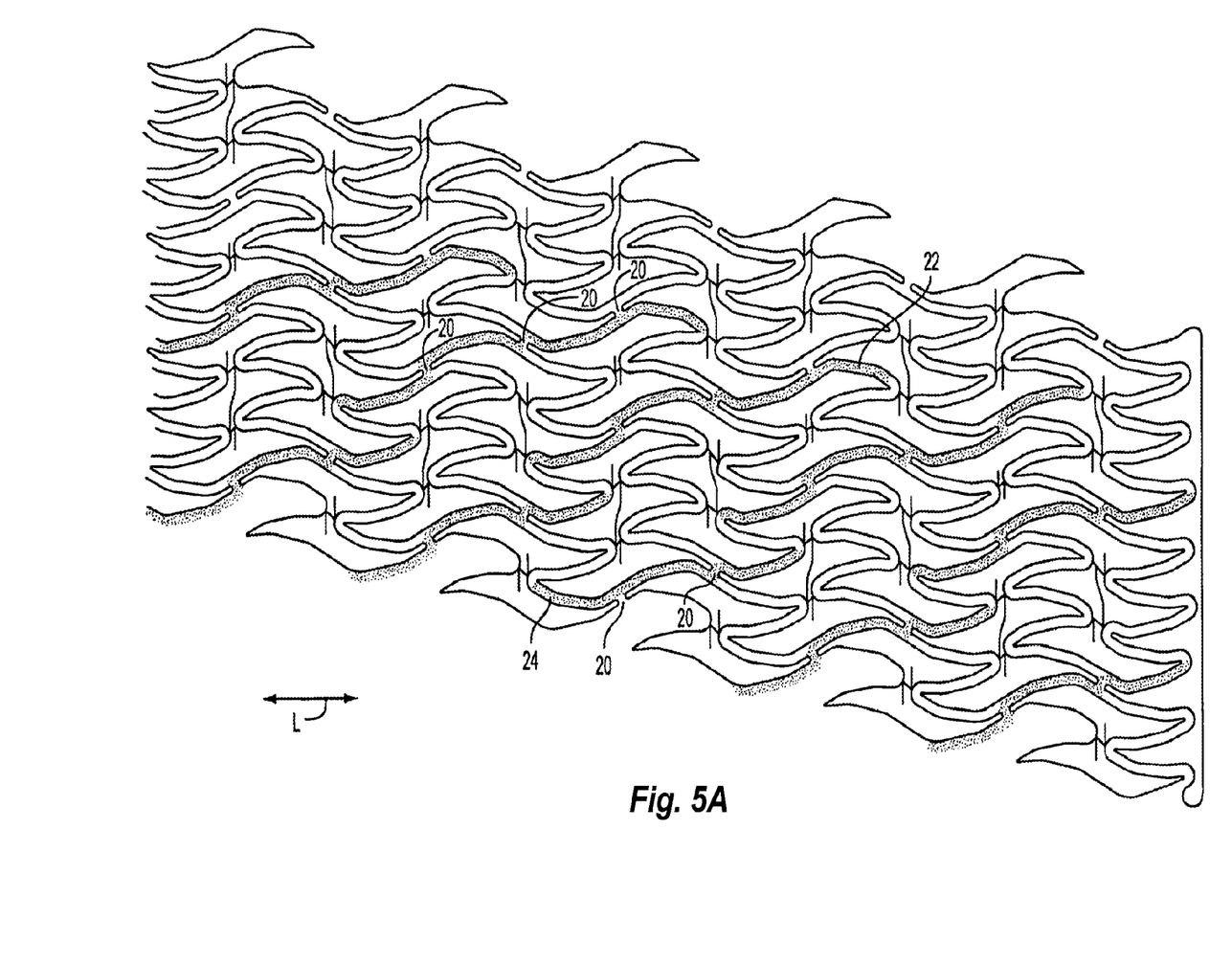
FIGS. 5A and 5B are views of further alternative embodiments of the stent of the present application having different interconnection patterns.
Figure 5B:
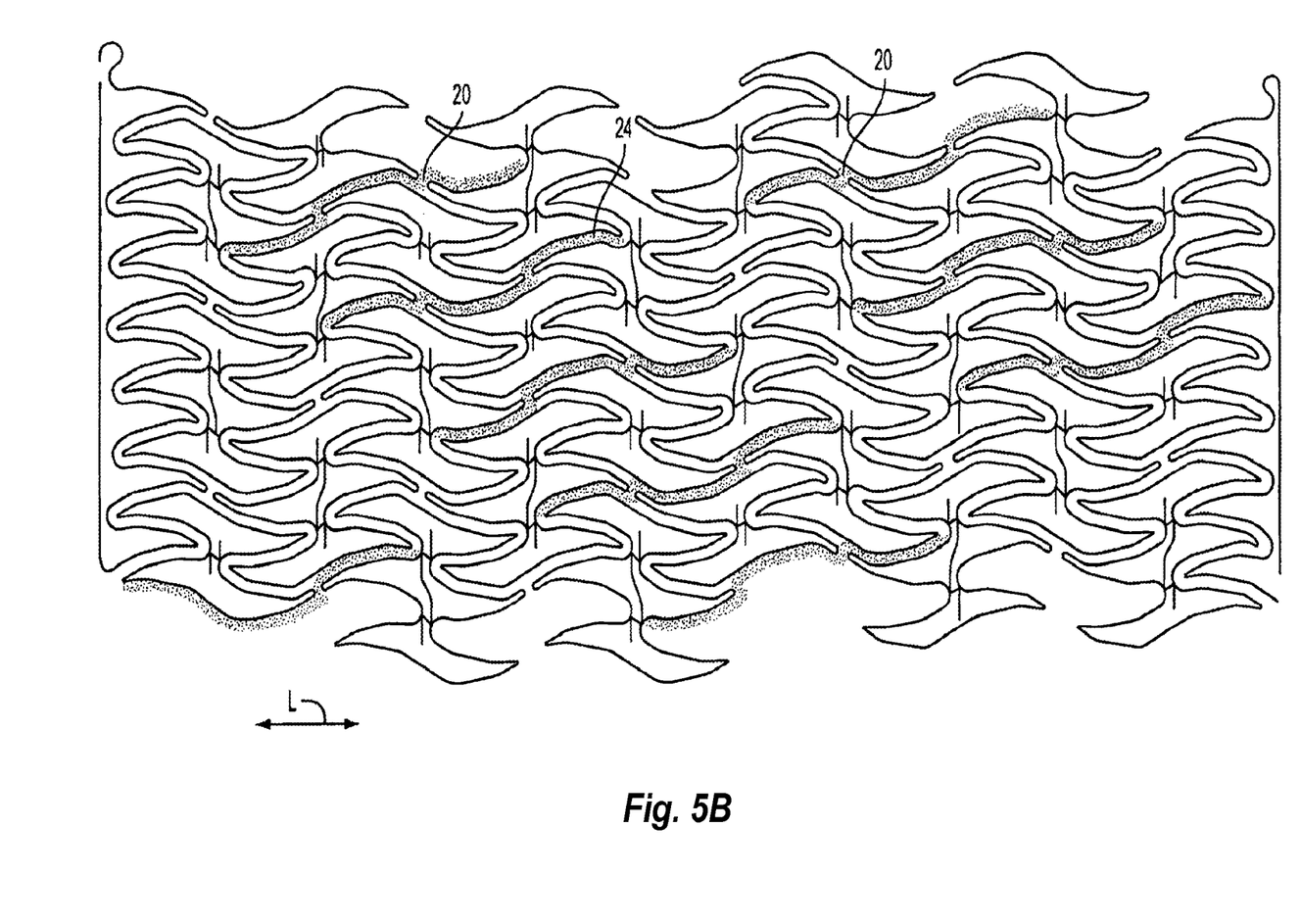

In FIGS. 5A and 5B, additional embodiments of web structures of the present invention, in which line L indicates the direction of the longitudinal axis of the stent. In the embodiment of FIG. 5A, integral transition sections 20 are arranged in a pattern so that the transition sections span either four or three adjacent webs. For example, the portion indicated as 22 in FIG. 5A includes three consecutively joined transition sections, spanning four webs. In the circumferential direction, portion 22 alternates with the portion indicated at 24, which includes two consecutive transition sections, spanning three webs.

The stent according to the present embodiment may be designed to be balloon expandable or self-expanding, and may be manufactured from a variety of materials, including polymeric materials, for example poly-L-lactid materials, or metallic materials or metal alloys, for example stainless steel, titanium, platinum, tantalum, titanium alloys, platinum alloys, nickel-titanium alloys such as Nitinol, platinum-Nitinol alloys, tantalum alloys, cobalt-chromium alloys or combinations of the above mentioned materials and alloys. Additionally, the stent according to the present embodiment may be manufactured with single or multiple layer structures, for example, with a two or three layer structure.

The stent according to the present embodiment also is preferably radiopaque, in order to facilitate insertion and positioning into a vessel or organ by a clinician, and may comprise a therapeutic agent, such as a therapeutic agent for retarding thrombus formation or restenosis, or a therapeutic agent for systemic or local delivery via the blood system.

Although preferred illustrative embodiments of the present invention are described hereinabove, it will be evident to one skilled in the art that various changes and modifications may be made therein without departing from the invention. It is intended in the appended claims to cover all such changes and modifications that fall within the true spirit and scope of the invention.

What is claimed is:

1. A stent comprising:
   a tubular body having a longitudinal axis, and having a proximal, a distal end, and a lumen extending longitudinally therebetween, and a wall having areas thereof removed to define a web structure configured for circumferential expansion from a contracted delivery configuration to an expanded deployed configuration;
   the web structure comprising a plurality of web patterns interconnected with one another at a plurality of X-shaped transition sections, and that are arranged so that the web patterns are situated side-by-side along the longitudinal length of the tubular body, with each web pattern also extending circumferentially around the wall;

at least one of said interconnected web patterns comprising, at least three webs joined end-to-end so as to extend between a first pair of X-shaped transition sections with no intervening X-shaped transition sections between the first pair of X-shaped transition sections;

said three webs that are joined end-to-end being joined by two bends so that the bends permit the three webs to be generally foldable between the first pair of X-shaped transition sections when said tubular body is in the contracted delivery configuration, and then unfolded when said tubular body is expanded to the deployed configuration;

a single web connected between a second pair of X-shaped transition sections with no intervening X-shaped transition sections between the second pair of interconnection locations; and said at least three webs each comprising a plurality of web sections, with one of the web sections being angled relative to one other web section when the stent is in the expanded deployed configuration.

2. The stent of claim 1, wherein the X-shaped transition sections are disposed at an angle relative to a longitudinal axis of the stent.

3. The stent of claim 2, wherein each X-shaped transition section is formed by a junction between the upward end of a bend interconnecting two struts with a downward end of a bend interconnecting two other struts.

4. The stent of claim 1, wherein the X-shaped transition sections connect one out of every three pairs of adjacent bends around the circumference of the web patterns.

5. The stent of claim 4, wherein the X-shaped transition sections extending from one end of each web pattern are staggered relative to the X-shaped transition sections extending from an opposite end of the web pattern.

6. The stent of claim 1, wherein the stent is formed using a material so that the stent is balloon expandable when deployed.

7. The stent of claim 6, wherein the stent is manufactured from a deformable material.

8. The stent of claim 7, wherein the deformable material is chosen from the group consisting of stainless steel and titanium.

9. The stent of claim 1, wherein the stent is formed using a shape memory alloy so that the stent is self-expanding when deployed.

10. The stent of claim 1, wherein the stent is manufactured from a polymeric material, a metallic material, or a metal alloy.

11. The stent of claim 10, wherein the polymeric material is a poly-L-lactid material.

12. The stent of claim 10, wherein the metallic material is stainless steel, titanium, platinum, tantalum, or a combination thereof.

13. The stent of claim 10, wherein the metal alloy is a titanium alloy, a platinum alloy, a nickel-titanium alloy, a platinum-nickel-titanium alloy, a tantalum alloy, a cobalt-chromium alloy, or a combination thereof.

14. The stent of claim 1, wherein at least a portion of the stent comprises a radiopaque material.

15. The stent of claim 1, wherein the web structure comprises a therapeutic coating.

16. The stent of claim 15, wherein the therapeutic coating is selected from the group consisting of therapeutic agents that retard thrombus formation, therapeutic agents that retard restenosis, and therapeutic agents for systemic or local delivery via the blood system.

17. The stent of claim 1, wherein the stent is manufactured as a single layer structure.

18. The stent of claim 1, wherein the stent is manufactured as a multi-layer structure.

19. A stent comprising:

a tubular body having a longitudinal axis, and having a proximal end, a distal end, and a lumen extending longitudinally therebetween, and a wall having areas thereof removed to define a web structure configured for circumferential expansion from a contracted delivery configuration to an expanded deployed configuration;

the web structure comprising a plurality of web patterns interconnected with one another at a plurality of X-shaped transition sections, and that are arranged so that the web patterns are situated side-by-side along the longitudinal length of the tubular body, with each web pattern also extending circumferentially around the wall;

at least three webs joined end-to-end so as to extend between a first pair of X-shaped transition sections with no intervening X-shaped transition sections between the first pair of X-shaped transition sections;

said three webs that are joined end-to-end being joined by two bends so that the bends permit the three webs to be generally foldable between the first pair of X-shaped transition sections when said tubular body is in the contracted delivery configuration, and then unfolded when said tubular body is expanded to the deployed configuration;

a single web connected between a second pair of X-shaped transition sections with no intervening X-shaped transition sections between the second pair of interconnection locations; and each web comprising three web sections, with one of the web sections being a central section joined at opposite ends thereof to two lateral sections, each of the lateral sections being angled relative to the central section when the stent is in the expanded deployed configuration.

20. The stent of claim 19, wherein each of the struts comprises three substantially straight sections.

21. The stent of claim 19, wherein each X-shaped transition section is disposed at an angle relative to a longitudinal axis of the stent.

22. The stent of claim 21, wherein each X-shaped transition section is formed by a junction between an upward end of a bend interconnecting two struts with a downward end of a bend interconnecting two other struts.

23. The stent of claim 19, wherein the X-shaped transition sections connect one out of every three pairs of adjacent bends around the circumference of the web pattern.

24. The stent of claim 23, wherein the X-shaped transition sections extending from one end of each web pattern are staggered relative to the X-shaped transition sections extending from an opposite end of the web pattern.

25. The stent of claim 19, wherein the stent is formed using a material so that the stent is balloon expandable when deployed.

26. The stent of claim 25, wherein the stent is manufactured from a deformable material.

27. The stent of claim 26, wherein the deformable material is chosen from the group consisting of stainless steel and titanium.

28. The stent of claim 19, wherein the stent is formed using a shape memory alloy so that the stent is self-expanding when deployed.

29. The stent of claim 19, wherein the stent is manufactured from a polymeric material, a metallic material, or a metal alloy.

30. The stent of claim 29, wherein the polymeric material is a poly-L-lactid material.

31. The stent of claim 29, wherein the metallic material is stainless steel, titanium, platinum, tantalum, or a combination thereof.

32. The stent of claim 29, wherein the metal alloy is a titanium alloy, a platinum alloy, a nickel-titanium alloy, a platinum-nickel-titanium alloy, a tantalum alloy, a cobalt-chromium alloy, or a combination thereof.

33. The stent of claim 19, wherein at least a portion of the stent comprises a radiopaque material.

34. The stent of claim 19, wherein the web structure comprises a therapeutic coating.

35. The stent of claim 34, wherein the therapeutic coating is selected from the group consisting of therapeutic agents that retard thrombus formation, therapeutic agents that retard restenosis, and therapeutic agents for systemic or local delivery via the blood system.

36. The stent of claim 19, wherein the stent is manufactured as a single layer structure.

37. The stent of claim 19, wherein the stent is manufactured as a multi-layer structure.

38. A stent comprising:
- a tubular body having a longitudinal axis, and having a proximal end, a distal end, and a lumen extending longitudinally therebetween, and a wall having areas thereof removed to define a web structure configured for circumferential expansion from a contracted delivery configuration to an expanded deployed configuration;
- the web structure comprising a plurality of web patterns interconnected with one another at a plurality of X-shaped transition sections, and that are arranged so that the web patterns are situated side-by-side along the longitudinal length of the tubular body, with each web pattern also extending circumferentially around the wall;
- at least one of said interconnected web patterns comprising,
- at least three webs joined end-to-end so as to extend between a first pair of X-shaped transition sections with no intervening X-shaped transition sections between the first pair of X-shaped transition sections;
- said three webs that are joined end-to-end being joined by two bends so that the bends permit the three webs to be generally foldable between the first pair of X-shaped transition sections when said tubular body is in the contracted delivery configuration, and then unfolded when said tubular body is expanded to the deployed configuration;
- a web connected between a second pair of X-shaped transition sections with no intervening X-shaped transition sections between the second pair of interconnection locations; and
- each of said at least three webs comprising a plurality of web sections, with one of the web sections being angled relative to one other web section when the stent is in the expanded deployed configuration.

* * * * *